United States Patent [19]

Avila et al.

[11] Patent Number: 4,934,199
[45] Date of Patent: Jun. 19, 1990

[54] METHOD AND APPARATUS FOR PREPARING SPECIMENS FOR DESTRUCTIVE TESTING OF GRAPHITE EPOXY COMPOSITE MATERIAL

[75] Inventors: Steven J. Avila, Federal Way; Charles R. Reid, Seattle, both of Wash.

[73] Assignee: Boeing Company, Seattle, Wash.

[21] Appl. No.: 173,485

[22] Filed: Mar. 25, 1988

[51] Int. Cl.⁵ .............................................. G01N 1/28
[52] U.S. Cl. .................................. 73/863; 73/864.41; 83/919; 156/256
[58] Field of Search ............... 73/863, 864.41; 83/919, 83/664; 156/256

[56] References Cited

U.S. PATENT DOCUMENTS

| | | | |
|---|---|---|---|
| 3,227,024 | 1/1966 | Krebs | 83/919 X |
| 3,791,903 | 2/1974 | Omi et al. | 156/256 X |
| 3,977,449 | 8/1976 | Sadashige | 156/256 X |
| 4,006,051 | 2/1977 | Board, Jr. | 156/256 X |
| 4,517,040 | 5/1985 | Whitted | 156/256 X |
| 4,629,629 | 12/1986 | David | 426/482 |

FOREIGN PATENT DOCUMENTS

| | | | |
|---|---|---|---|
| 45194 | 4/1979 | Japan | 73/864.41 |
| 107935 | 8/1980 | Japan | |
| 15137 | 1/1988 | Japan | 73/863 |
| 1067465 | 1/1984 | U.S.S.R. | 73/864.41 |
| 1355894 | 11/1987 | U.S.S.R. | 73/864.41 |
| 1190944 | 5/1970 | United Kingdom | 73/864.41 |

OTHER PUBLICATIONS

English Abstract of Japanese Patent Document No. 55-10793S by *Patent Abstracts of Japan;* ABS Grp, No. P035, Abs. vol. No. 4, No. 160, ABS Pub. Date Nov. 8, 1980 (Patent Document Published Aug. 19, 1980).

*Primary Examiner*—Tom Noland
*Attorney, Agent, or Firm*—Seed and Berry

[57] ABSTRACT

A method of preparing specimens of composite material for destructive testing is disclosed. A panel from which the specimens are to be cut is cut from a sheet of composite material. The panel is cut from the sheet by first cutting the sheet along a line to form an alignment edge. The alignment edge is placed against a fence and the panel is cut with a first saw blade to a predetermined width and length. A first set of pads is placed on a fitting, the pads being spaced apart by a predetermined distance by a plurality of pins extending from the fitting. The panel is placed on top of the pads. A second set of pads is placed on top of the panel. The fitting is clamped to a table. The table moves into the path of a second saw blade which cuts the panel in a first direction. The fitting is rotated and the table is moved into the path of the second saw blade again to cut the specimens. The smoothness of the surface cut by the second saw blade is significantly smoother than the smoothness of the first saw blade. Providing smooth surfaces on the specimen aids in ensuring that destructive testing of the specimen provides an accurate measure of the quality of the material.

14 Claims, 8 Drawing Sheets

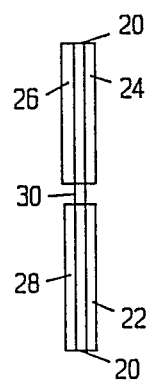
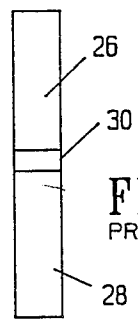
FIG.1 PRIOR ART
FIG.2 PRIOR ART
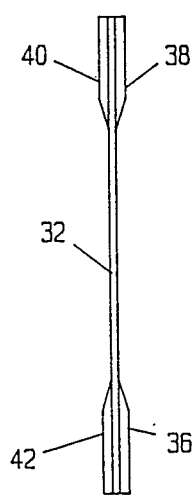
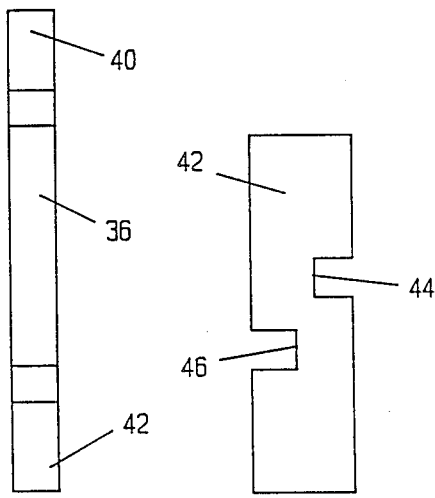
FIG.3 PRIOR ART
FIG.4 PRIOR ART
FIG.5 PRIOR ART

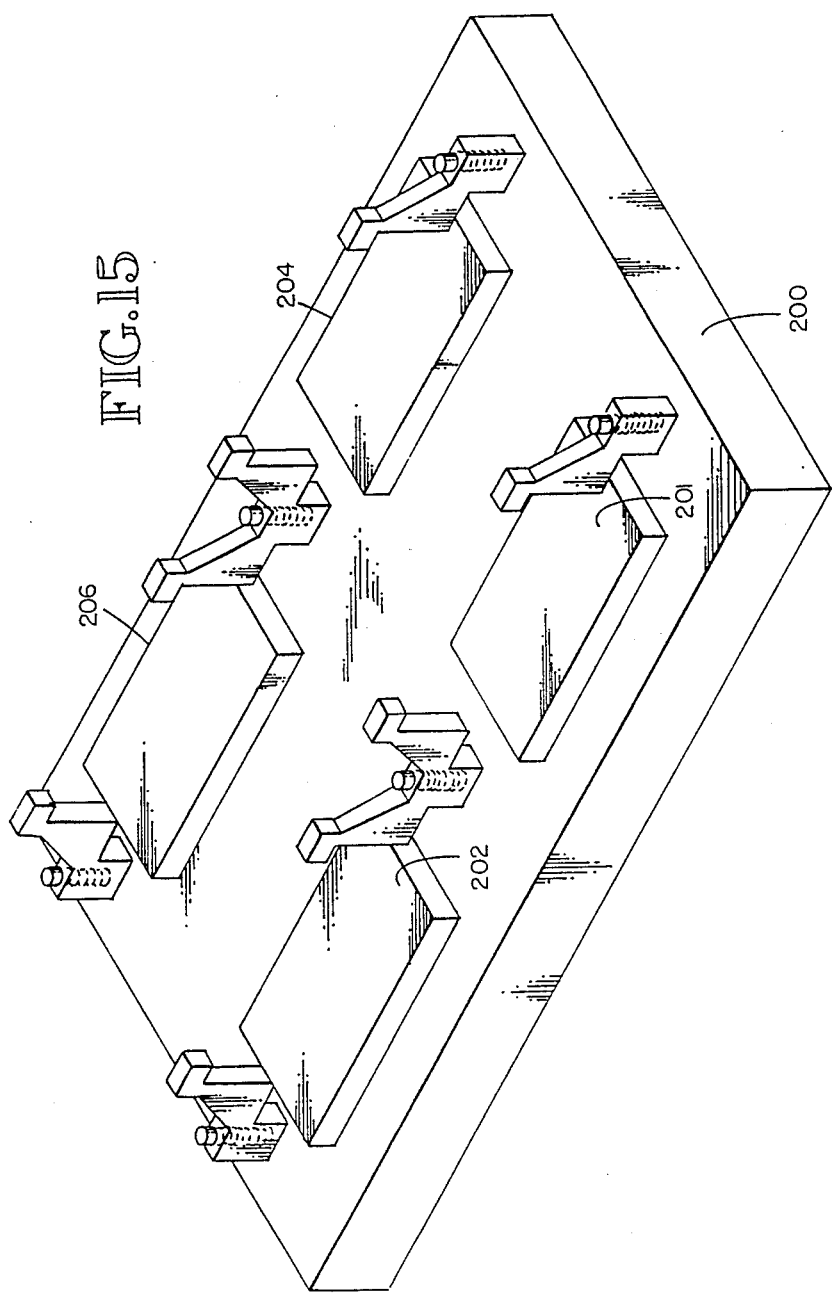

METHOD AND APPARATUS FOR PREPARING SPECIMENS FOR DESTRUCTIVE TESTING OF GRAPHITE EPOXY COMPOSITE MATERIAL

TECHNICAL FIELD

This invention relates to preparation of specimens of graphite epoxy composite material for destructive testing and more particularly to a method of preparing samples in production volume quantities that are highly uniform to each other and to the apparatus for preparing these samples.

BACKGROUND ART

Aircraft structures are increasingly being constructed from a graphite epoxy composite material. It is often desirable to test samples of the material from each lot of material produced or purchased. The sheets of graphite fiber from which the composite material is produced are made by third parties. When the purchaser of the material receives a shipment including several lots of graphite fiber sheets, the purchaser often conducts tests to determine if the purchased graphite fiber meets the required specifications.

One method of testing the graphite fiber is to produce test specimens using specifications similar to the specifications that will be used in producing the material for use on the aircraft structure. After the specimens are prepared, they are subjected to various tests, including destructive tests. These tests include tensile tests in which the specimen is placed in tension and the load increased until the member fails. A compression test is also frequently performed in which the member is placed in compression and the load increased until the member fails. The amount of load held by the member until failure is an indication of the strength of the material. If the specimen fails under a small load this indicates that the sheets of material as purchased are defective, even though the proper steps in producing the final product were followed.

It is important that the testing of the specimens be accurate in all respects to ensure that the material is the safe for use on an aircraft. A problem in the prior art is difficulty of producing specimens that are uniform each time. The specimens are prepared from a larger sheet taken from the lot. This usually requires that the sheet be cut from the lot and other preparations performed on the sheet. It is possible to damage a specimen when cutting it from a larger sheet such that the load carried by the specimen is not indicative of the load that can be carried by that lot of material if properly prepared. Other specimens prepared from the same lot may fail under very different load conditions, thus indicating that procedures followed in preparing the specimens are important.

SUMMARY OF THE INVENTION

It is therefore an object of this invention to provide a method of preparing specimens for testing that ensures that the specimens are representative of the characteristics of the lot from which the material was taken.

It is an object of this invention to provide a method of cutting specimens from a sheet of composite material that are uniform with respect to each other.

It is another object of this invention to provide an apparatus for cutting specimens from the sheet which ensures that the specimens are uniform with respect to each other.

It is another object of this invention to provide an apparatus for preparing specimens taken from sheets.

It is another object of this invention to provide a fitting for holding specimens while being prepared to ensure that they are uniformly prepared and cut with respect to each other.

These and other objects of the invention are accomplished by cutting the material along a grain line to form an alignment edge. The material is cut to a predetermined size. This is accomplished on a production basis by using a fence at a fixed location and placing a spacer of a desired width in-between the fence and the saw. If a different size of material is needed, the fence is left in its initial position and a different spacer is placed in position. After the material is cut to the proper dimensions, it is ready to be bonded to the test pads. To ensure that the test pads are bonded in the correct location, the pads are placed on a fitting and aligned with pins on the fitting. The pads are spaced an exact distance apart by abutting them against pins positioned on the fitting. The material is then placed on the fitting. A second set of pads are then placed on top of the material. The pads and material are then bonded together.

After the pads and material have been properly bonded, the material is cut into the proper dimensions to form the specimens. It is critical that the edges have a smooth finish when the final test is performed to ensure a uniform testing result. The saw which performs the final cutting is aligned using a series of spacer members and washers to ensure a smooth, accurate cut. The specimens are then tested.

BRIEF DESCRIPTION OF THE DRAWINGS

FIG. 1 is a side elevation of a compression sample.

FIG. 2 is a top plan of the compression sample of FIG. 1.

FIG. 3 is a side elevation of a tensile sample.

FIG. 4 is a top plan of the tensile sample of FIG. 3.

FIG. 5 is a side plan of a notch sample.

FIG. 15 is an isometric view of the cutting table of the present invention

DETAILED DESCRIPTION OF THE INVENTION

Figure 6:
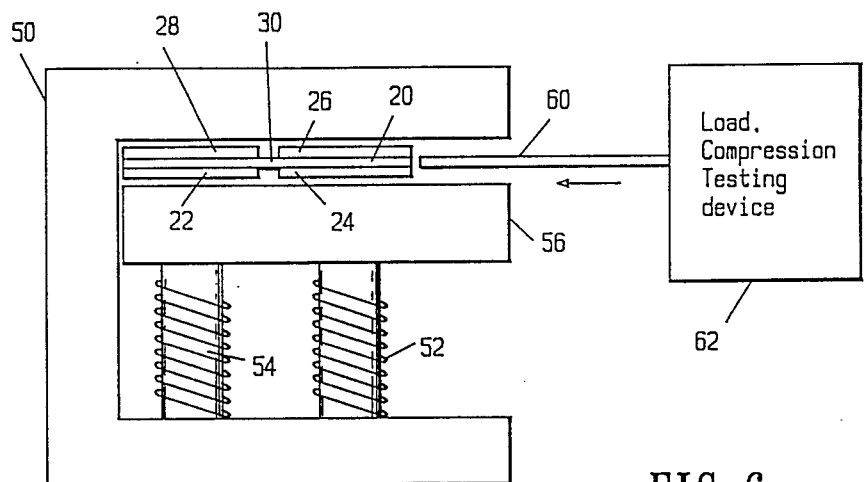
FIG. 6 is a side elevation of a compression test.

The samples of the specimens of composite material to be tested are shown in FIGS. 1 through 5. A compression specimen 20 having 22, 24, 26 and 28 is shown in FIGS. 1 and 2. The specimen includes a region 30 which will be the region which fails under the compression test. A tensile specimen 32 having pads 34, 36 38 and 40 is shown in FIGS. 3 and 4. The tensile specimen is gripped at the pads and placed in tension until failure. A notch specimen 42 having notches 44 and 46 is shown in FIG. 5. The notch specimen has no pads. The notch specimen may be placed in either compression or tension and loaded until failure. Usually, the region between the notches fails first.

The specimens of FIGS. 1–5 must be made to uniform and exact specifications to yield valid results in the test. For example, the specimens must be exactly flat to a high degree of tolerance. Further, the space between the pads on the compression and tensile specimens must be exact to a very tight tolerance. For example, the space between the pads on the compression specimen must be, in some specifications, 0.188 inches plus or minus 0.003 inches. Even tighter tolerances are required for the placement and depth of the notches on the notch specimens.

Previous to this invention, it was very difficult to produce specimens uniform with respect to each other. The tolerances are very tight and it was difficult to produce specimens according to these tolerances. For example, prior to this invention, an average of 5 specimens per hour could be produced by two people. Using the invention, a single worker can produce 10 perfect specimens in ten minutes. Further, each specimen is exactly accurate and uniform and will always provide uniform test results.

A compression test on a compression sample is shown in FIG. 6. A vise 50, having threaded screw members 52 and 54, clamps the specimen in position in the vise 50. Anvil 56 abuts against the pads 22 and 24 to firmly grip the sample. A compression testing device 62 having a compression rod 60 abuts the end of the specimen 20 to apply compression. The compression load is increased until the sample fails. If the sample is properly constructed, the load at which the sample fails is an accurate indication of the strength of the sample. If the specimen is not properly constructed, the load at which the specimen fails is not conclusive and further tests must be performed. One major problem in the prior art is that it was difficult to determine whether a failure under a light load was due to faulty materials and specifications or due to an improperly constructed specimen.

Figure 7:
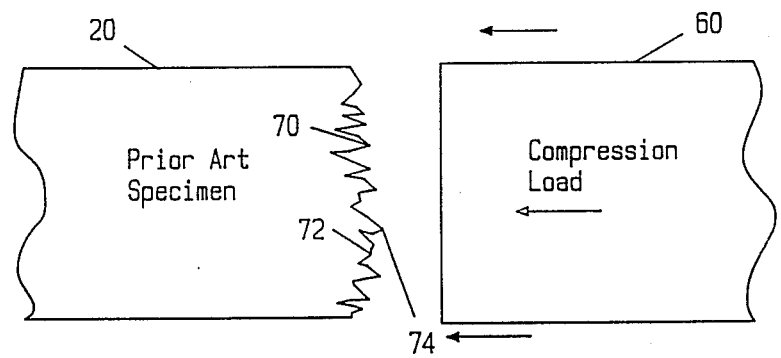
FIG. 7 is an enlarged side elevation of a compression test using a sample produced according to the methods and machines taught by the prior art.

A prior art compression specimen is shown in an enlarged view in FIG. 7. The end of the specimen has a relatively rough finish. Prior to this invention, this was the best finish that could be achieved on most specimens. The roughness shown corresponds to a surface finish in the range of 230 to 150 RMS according to industry standard surface roughness values. When the compression test is performed, the compression piston 60 contacts the extended portions of the specimen first, such as points 70, 72 and 74. These points all bear the load of the compression test. When the composite graphite fibers at these points fails, the entire part quickly fails and is completely destroyed. The structure of the graphite epoxy composite structure is particularly unique in the way that the fibers carry load and have no yield. The extended fibers at points 70, 72 and 74 may not yield appreciably until they fail. In a metal part, some deformation would take place prior to failure, but in a graphite epoxy part, when one or two of the fibers in the member fail, the entire part disintegrates in an explosion. If the finish is not smooth, the specimen may fail under very light loads. The part is now destroyed however and it is not possible to determine what caused the failure.

Other parts made at the same time may have a considerably different grade of finish and thus the load upon failure was more dependent on the specimen preparation rather than on the quality of the materials used. For example, according to the prior art, considerable effort was expended to ensure that the finish at the end to which the compression was applied was exactly smooth and aligned. Various sanders, grinders and other smoothing devices were used. These often resulted in parts which were sloped or were not the proper finish. The best finish achieved was usually greater than a 32 RMS. Even with a 32 RMS finish, the compression specimen is having the load applied to less than 75% of the fibers.

Figure 8:
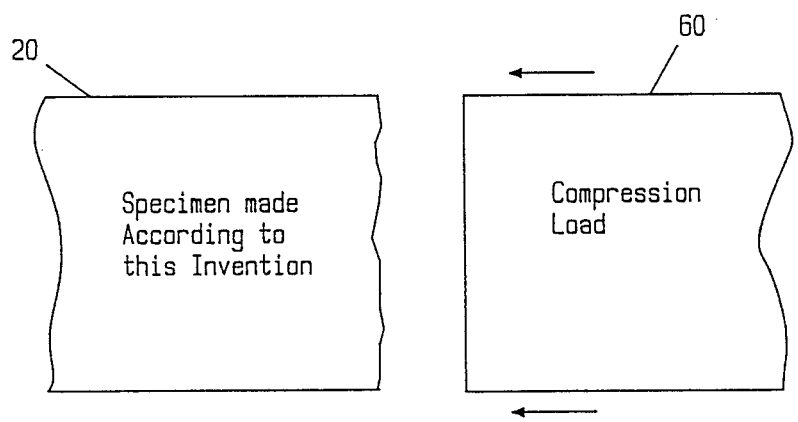
FIG. 8 is an enlarged side elevation of a compression test using a sample produced according to the invention.

According to the invention, a very smooth surface is provided for the compression test to be performed as shown in FIG. 8. The surface finish has an 15 RMS or less. This corresponds to in excess of 95% of the surface of the specimen being in contact with the compression load ram 60 during a compression test. This results in more accurate load reading results than was previously possible.

Similar problems occur for tensile and notch specimens. The finish on all surfaces is critical in obtaining an accurate test in tensile and notch specimens.

Figure 9:
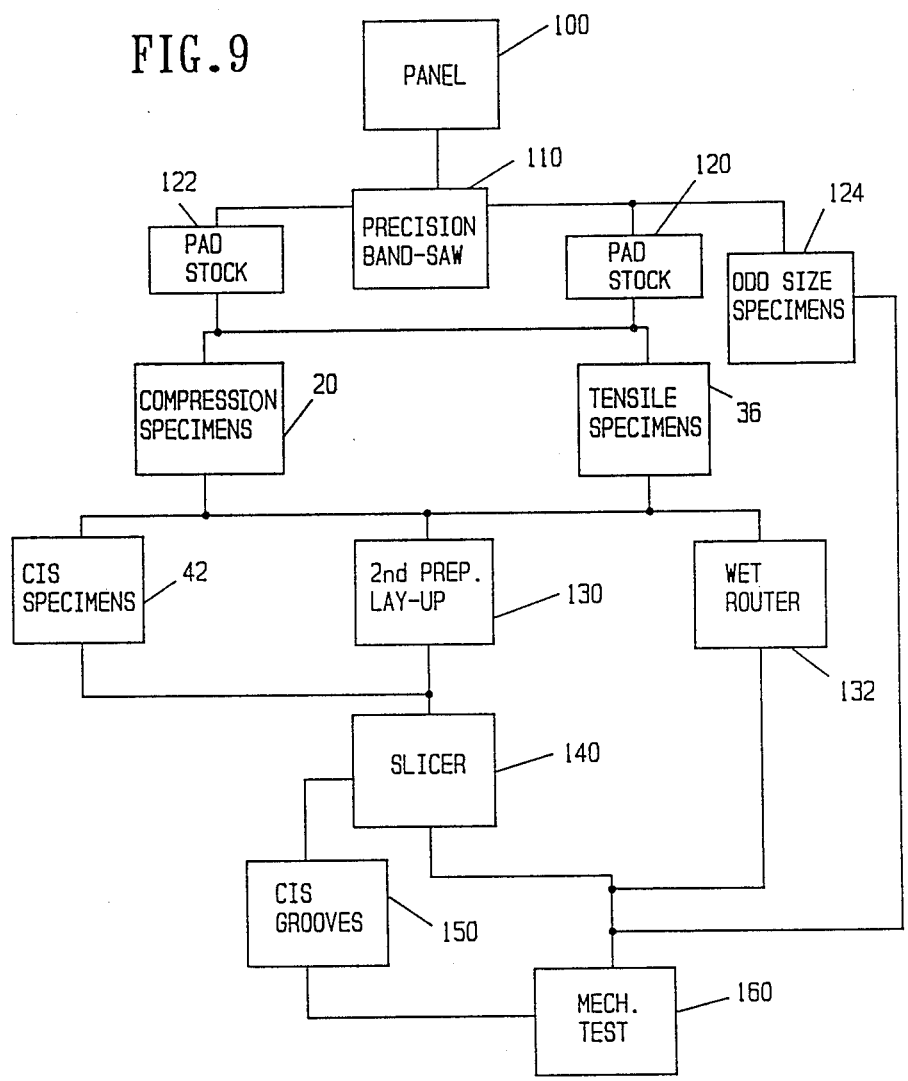
FIG. 9 is a flow diagram of the production of samples according to the invention.

The steps followed in producing specimens according to the invention are illustrated in the flow diagram of FIG. 9. The panel 100 is provided from the lot of material. The panel 100 is then precision cut to a proper size for the fitting by the band saw 110. The band saw 110 does not cut the material with sufficient smoothness for use in the final test but does cut the parts to sufficient precision to use in the fitting. The pads 22–28 and 36–42 are then cut from the correct pad stock, 122 and 120 respectively. The pads are also cut using the band saw, but using different spacers.

The pads and specimens are then placed on the proper fitting and bonded together in a second preparation or lay-up operation 130. The notched specimens 42 of FIG. 5 are represented as CIS specimens in the flow diagram of FIG. 9. These specimens do not have bond pads and are placed on a fitting for cutting by the slicer. After being cut to the proper dimensions with the correct finish by the slicer, the notches or grooves are placed in the CIS specimens as shown at 150. The other specimens are cut by the slicer 140 after being properly bonded and are then tested at the mechanical load test 160. Some specimens may be odd-shaped or odd sized as illustrated at 124. Other specimens may require certain notches or grooves to be made at particular positions, and will be cut by the wet router 132. When the method as taught in FIG. 9 is followed using the particular equipment illustrated herein, the specimens are uniform in all respects and yield accurate testing results. The steps as outlined in FIG. 9 will now be described in more detail, including a description of the apparatus used at each stage of the invention.

Figure 10:
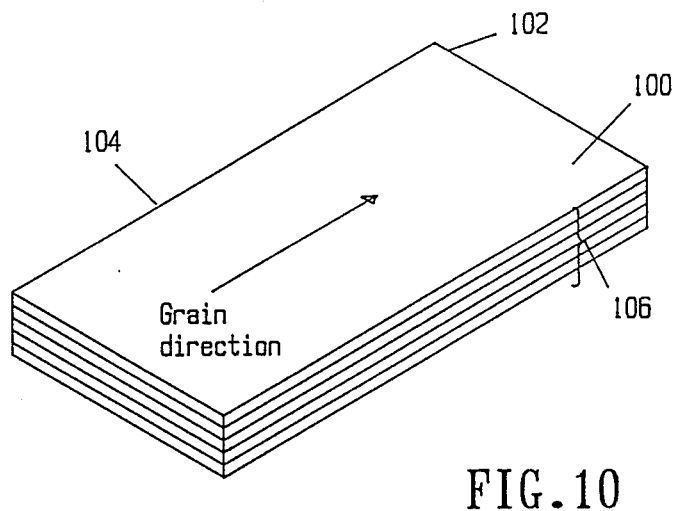
FIG. 10 is an isometric view of a panel prior to preparing specimens.

The beginning panel 100 has a grain direction as indicated by the arrow in FIG. 10. The panel 100 is usually a sandwich of many layers of composite material, usually 8 to 10 layers. Five layers 106 are shown but the panel may be comprised of from 2 to 20 or more layers. The grain direction will be similar to the length-wise direction of the panel, but will rarely be along the exposed edge. In order to ensure that the panel is aligned with the grain exactly, a notch, as at 102, is made in the panel 100. The panel is then split beginning at notch 102 towards the end. The panel will split along the natural grain line 104 and provide an exact alignment side to begin preparing the panel for cutting into specimens. Some panels do not have a grain direction and this step may be omitted for these panels.

Figure 11:
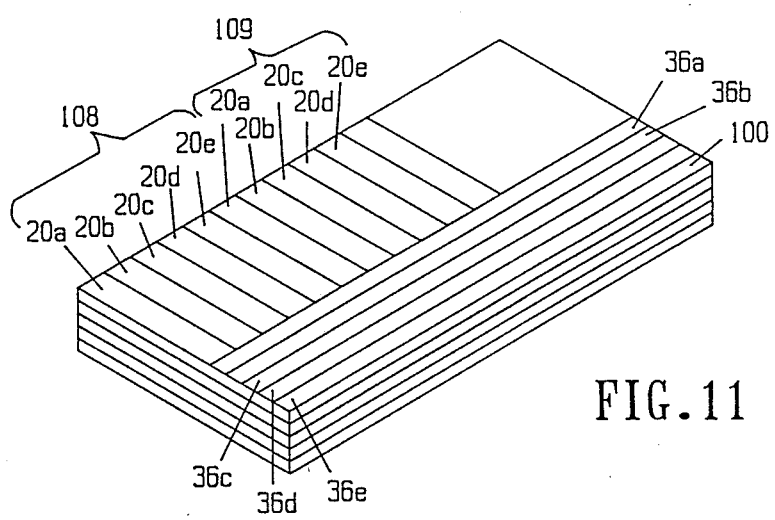
FIG. 11 is an isometric view of the panel of FIG. 10 illustrating the location of specimens cut from the panel.

The specimens that will be cut from the single panel 100 are illustrated in FIG. 11. Two coupons, 108 and 109, having five compression specimens 20a–20e and 20a'–20e' respectively when completed will be cut from the panel 100. Five tensile samples 36a–36e will also be cut from the panel 100.

Figure 12A:
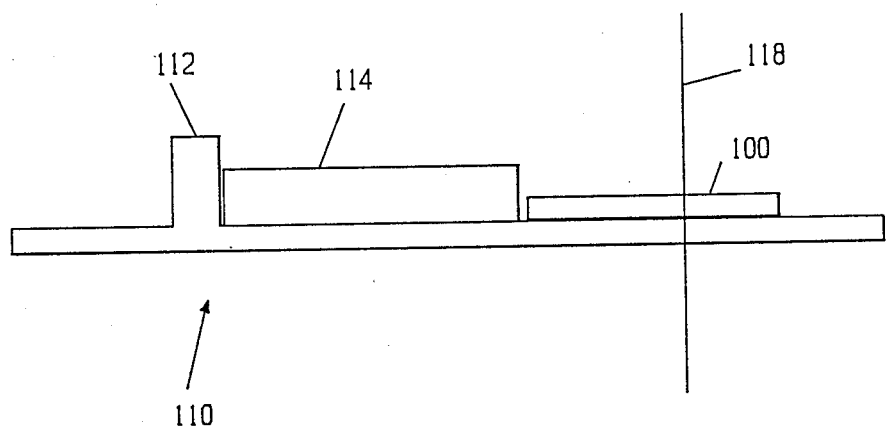
FIG. 12A is a side elevation of cutting the panel using a spacer and the band saw of the invention.
Figure 12B:
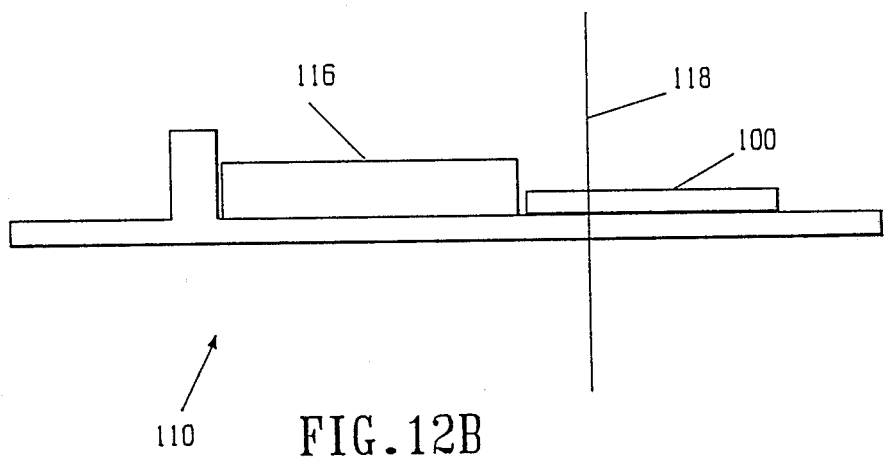
FIG. 12B is a side elevation of cutting the panel using a different spacer than shown in FIG. 12A with the same fence and band saw.

The precision band saw of the present invention is illustrated in FIGS. 12A and 12B. The precision band saw includes a saw blade 118 and a fence 112. A spacer 114 is placed between the fence and the band saw to exactly determine the width of the portion from the panel to be cut. The fence must be set with exact precision. It often takes a full day or more to set the fence to the exact precision required to produce proper specimens. If the fence is moved a few times a week, this becomes very time consuming. According to the present invention, the fence is placed at its most extended position. The exact distance is accurately determined in a short period of time. A series of spacers such as 114 and 116 are produced that will place the panel the correct distance from the fence. The spacers are produced with exact precision. After the proper spacers are made, the panel width to be cut can be varied several times a day without any extra time being consumed. The placement is accurate each time. The proper spacer is merely placed against the fence and the panel is cut by placing it against the spacer and moving it into the band saw.

Figure 13:
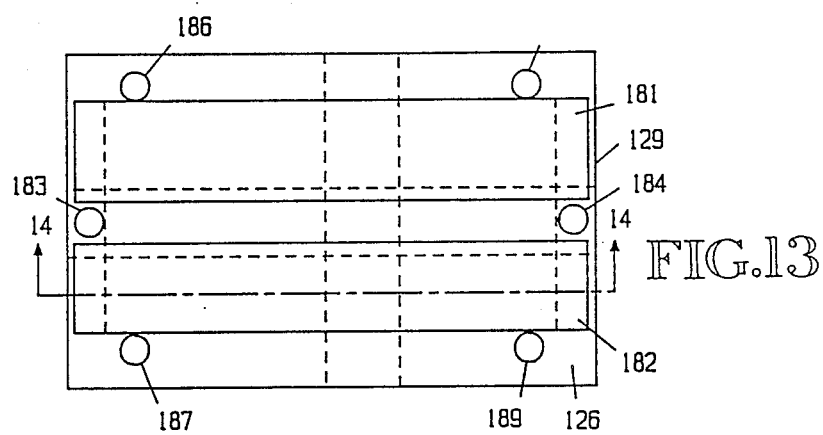
FIG. 13 is a top plan of the fitting of the invention.
Figure 14:
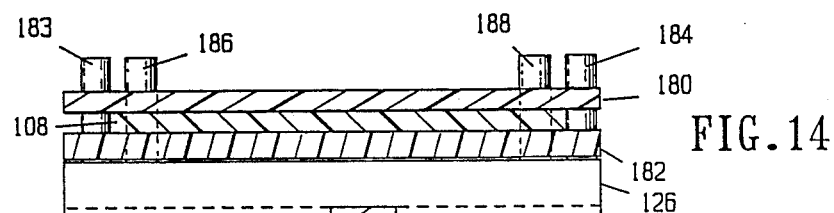
FIG. 14 is a cross section view taken along lines 14—14 of FIG. 13.

After the panel is cut into coupons 108 and 109, the coupons are placed on fittings 126 shown in FIGS. 13 and 14. The fittings 126 have pins 183 through 189 properly positioned to hold the pads and coupon 108 in position. The lower pad 182 is placed in the fitting 126. The pad 182 abuts along one edge against center pins 183 and 184. The pad 181 also abuts against center pins 183 and 184. These pins hold the pads an exact distance apart as required in the specimen. The coupon 108 is then placed on top of the pads 182 and 181. Top pads 180 and 179 are then placed on top of the coupon 108. The pads are held firmly in position while fitting is sent to lay-up to bond the pads to the coupon. This requires a heat treatment and several steps as is known in the art.

The fitting 126 has notches 128 and 129. These notches are used as keyways to position the fitting on keys 200, 202, 204 and 206 of the cutting table 200 of FIG. 15. One feature of the fitting 126 is that the notches are perpendicular to each other but notch 128 is offset from the center so that the fitting may not be placed on the cutting table 200 in the incorrect position.

Two fittings are placed on the cutting table 200 on keys 201 and 202. The cutting table is then moved into saw blades 220 and 222 of the slicer 140 of FIGS. 16 and 17. This cuts the edges to the required smoothness, a finish of 15 RMS, sufficient for the compression test. This cuts the ends of each of the five samples to be cut from coupon 108. The coupon 108 is then rotated 90 degrees and placed on key 206 using slot 128. The cutting table is then moved forward to cut the five specimens from the coupon using blades 224–234. The specimens are now ready to be tested.

Figure 16:
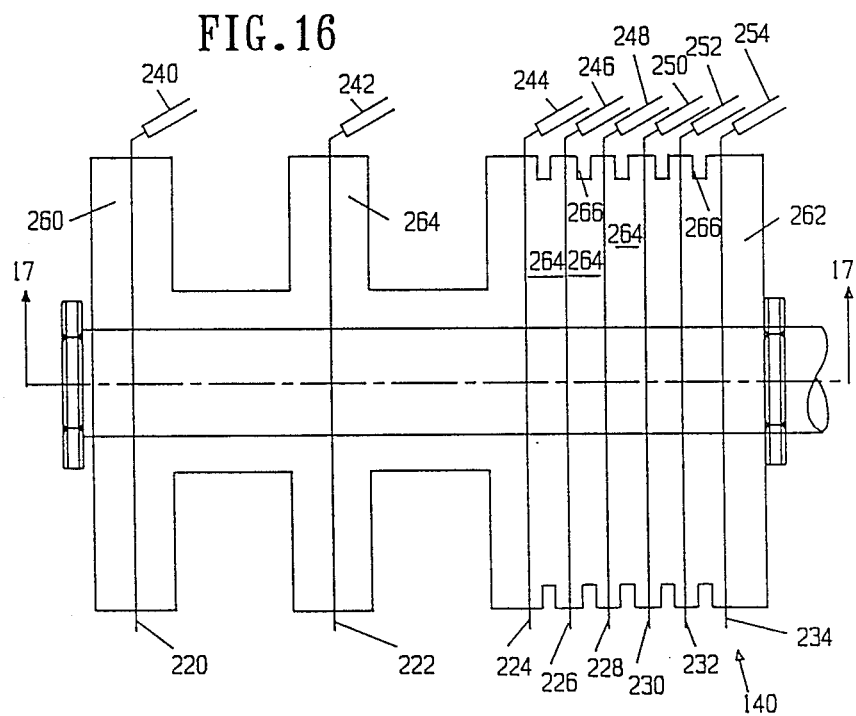
FIG. 16 is a side elevation of the gang saw of the present invention.

One significant feature of the slicer of FIG. 16 and other saws used in this invention is that wet saws having a stream of water 240–254 sprayed thereon are used in cutting the composite material. Prior to this invention, it was thought that composite material could not be cut with a wet cutting saw blade. The precision saws as described herein have been found to cut composite material to an unexpectedly smooth finish when used as wet cutting saw blades. The finish from the wet cutting saw blades of the present invention is smooth enough that additional polishing prior to testing is not necessary.

Figure 17:
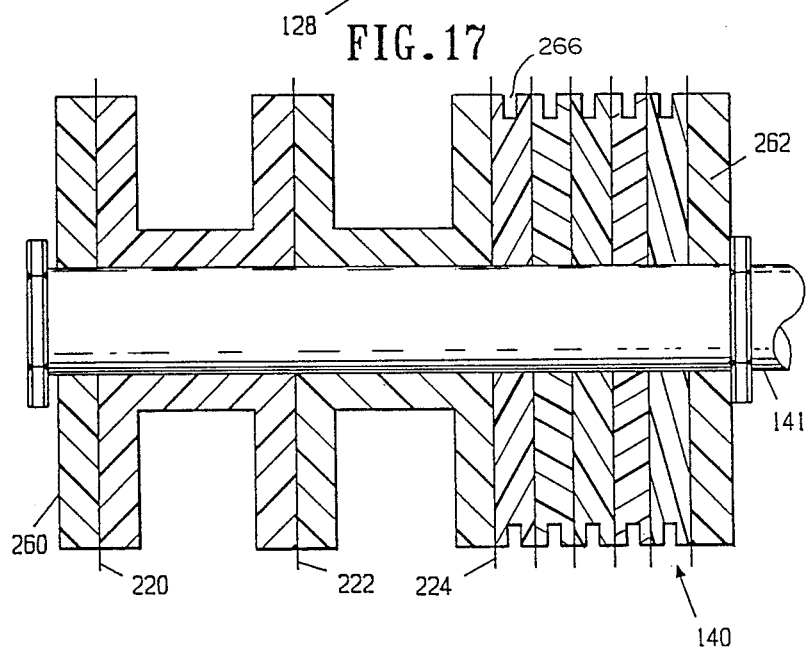
FIG. 17 is a cross sectional view of the gang saw of FIG. 16 along lines 17—17.

The washer 262 and 260 shown in FIGS. 16 and 17 provide an accurate, smooth cut not previously possible. The spacing members 264 extend along the entire surface areas of the saw blades except for that area necessary to cut into the material. This ensures that the wobble and misalignment of the saws are at a minimum. The groove 266 in the spacers 264 permit the pins of the fittings 126 to pass therethrough without being cut.

We claim:

1. The method of preparing a specimen of a composite material for testing comprising:
   cutting said material along a grain line to form an alignment edge;
   placing a spacer of a predetermined width between a fence and a saw blade;
   placing said alignment edge against said spacer;
   cutting said material to a predetermined width corresponding to the width of said spacer;
   placing a second spacer of a different width between said fence and said saw blade;
   cutting said material to a predetermined length corresponding to the width of said second spacer;
   placing a first set of pads on a fitting, said pads being spaced apart by a predetermined distance by a plurality of pins located between said pads;
   placing said material on top of said pads;
   placing a second set of pads on top of said material, said second set of pads being spaced apart a predetermined distance by a plurality of pins therebetween;
   affixing said sets of pads to said material;
   coupling said material and pads to a second fitting;
   cutting said material with a second saw in a first direction;
   rotating said fitting holding said material; and
   cutting said material in a second direction using a third saw to form said specimen for testing.

2. The method according to claim 1 further including applying a stream of water to said second saw while cutting said material.

3. The method according to claims 1 wherein said fitting has an alignment groove on the underside for aligning said fitting with respect to said second saw and a different alignment groove for aligning said fitting with respect to said third saw.

4. A method of preparing specimens of composite material for testing comprising:
   cutting said material to form an alignment edge;
   placing said alignment edge adjacent a fence with said material extending from said fence into the cutting path of a first saw blade;
   cutting said material with said first saw blade;

placing a first set of pads onto a fitting;
placing said material on top of said pads;
placing a second set of pads on top of said material;
affixing said first and second set of pads to said material;
securely coupling said fitting having said pads and said material thereon to a table for retaining said fitting; and
cutting said material with a second saw blade to form specimens for testing.

5. The method according to claim 4, further including the steps of:
removing said fitting from said table;
rotating said fitting with respect to said table;
securely coupling said fitting to said table in a second position; and
cutting said material in a second direction with said second saw blade to form specimens for testing.

6. The method according to claim 4 wherein said fitting is secured to said table with clamps.

7. The method according to claim 4 wherein said step of affixing said pads to said specimen includes a heat-treating step.

8. The method according to claim 4 wherein said fitting includes alignment pins and said pads abut against said pins for securing said pads in a selected position.

9. The method according to claim 4 wherein said table includes a key against which said fitting abuts to aid in aligning said fitting with respect to said second saw blade.

10. The method according to claim 9 wherein said fitting has a keyway extending inward from a bottom surface and said fitting abuts against said key by having said key within said keyway.

11. A method of preparing a specimen from a sheet of composite material comprising:

cutting a panel of composite material from said sheet of composite material using a first saw, said panel having a first shape, preselected dimensions and first cut surface along the surface cut by said first saw to seperate said panel from said sheet, said first cut surface having a first smoothness;
coupling said panel to a fitting to securely hold said panel in a preselected position on said fitting;
coupling said fitting to a table to securely hold said fitting in a preselected position on said table; and
cutting a specimen from said panel using a second saw while said fitting is coupled to said table, said fitting and said table providing an exact positioning of said panel with respect to said second saw blade, said specimen having a second shape, preselected dimensions, and a second cut surface along the surface cut by said second saw to seperate said specimen from said panel, said second cut surface having a second smoothness, said second smoothness being smoother than said first smoothness.

12. The method of claim 11 wherein said step of coupling said panel to said fitting further includes the steps of:
coupling a first pad to a said fitting;
coupling said panel to said first pad to said fitting;
coupling a second pad to a top surface of said panel; and
affixing said first pad and said second pad to said panel to form a block coupled to said fitting having said panel sandwiched between said first pad and said second pad.

13. The method according to claim 8, further including:
moving said table into said saw blade for cutting said specimen.

14. The method according to claim 13 wherein said pads are affixed to said panel in a heat treatment step to form said unitary block of material.

* * * * *

UNITED STATES PATENT AND TRADEMARK OFFICE
CERTIFICATE OF CORRECTION

PATENT NO. : 4,934,199

DATED : June 19, 1990

INVENTOR(S) : Steven J. Avila et al.

It is certified that error appears in the above-identified patent and that said Letters Patent is hereby corrected as shown below:

In claim 13, column 8, line 32, delete "claim 8" and substitute therefor --claim 12--.

In claim 11, column 8, line 4, before "first cut" insert --a--.

Signed and Sealed this

Eighth Day of October, 1991

Attest:

HARRY F. MANBECK, JR.

Attesting Officer

Commissioner of Patents and Trademarks